United States Patent [19]
George

[11] Patent Number: 4,715,368
[45] Date of Patent: Dec. 29, 1987

[54] NOCTURNAL AIRWAY-PATENCY APPLIANCE

[76] Inventor: Peter T. George, Suite 520, 1441 Kapiolani Blvd., Honolulu, Hi. 96814

[21] Appl. No.: 893,584

[22] Filed: Aug. 6, 1986

[51] Int. Cl.⁴ .............................................. A62B 7/00
[52] U.S. Cl. ......................................... 128/136; 433/6
[58] Field of Search ..................... 433/6; 128/136, 421

[56] References Cited
U.S. PATENT DOCUMENTS 3,478,742 11/1969 Bohlmann ........................ 128/136
4,431,411 2/1984 Witzig et al. ............................. 433/6

Primary Examiner—Robert Peshock

[57] ABSTRACT

This invention is a unique and dentally supported intraoral device designed to prevent the occlusion of the oro-pharngeal airway which occurs while sleeping for patients with sleep apnea consisting of a one-piece dental mouthpiece with a front beak housing an orifice airway and custom-fitted anchoring molar and labial wire clasps and guide. It is one of the first solutions in the new field of pulmonary medical practice treating nocturnal breathing disorders.

1 Claim, 6 Drawing Figures

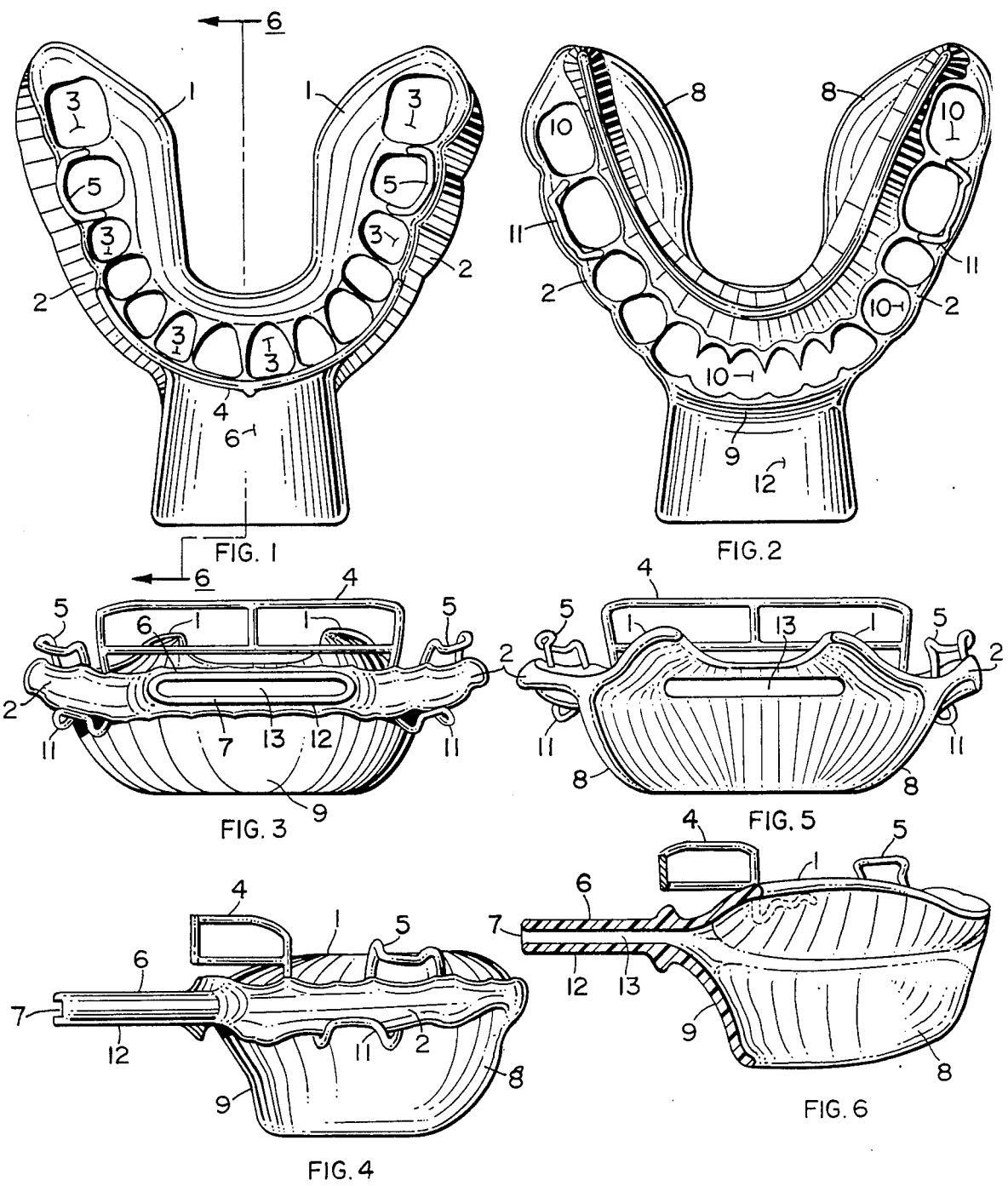

NOCTURNAL AIRWAY-PATENCY APPLIANCE

FIELD OF THE INVENTION AND BRIEF HISTORY

This invention is in the field of intra-oral devices designed to prevent occlusion of the oro-pharngeal airway which occurs while sleeping in patients with sleep apnea. The obstruction in Obstructive Sleep Apnea (OSA) occurs when the tongue is sucked back against the posterior pharangeal wall.

A brief history of Obstructive Sleep Apnea (referred hereafter as OSA) shows that the phenomena is only recently recognized by pulmonary physicians. Professional papers since 1982 describe researches on demography, the causes and effects of occlusion, its cost to the industry and to the patient the day after and related effects. The most common method of treatment of OSA to date has been surgical and drug therapies. My invention is the first device to treat OSA mechanically. It is a relatively inexpensive solution without any drug side effects or pre- and post-surgery complications, hospitalization or pains.

A thorough patent search from the Patent Office lists of all patents under the following Class/Subclasses has revealed no prior art or anything close to my invention. Under Subclass 623/09 for Prothesis of Larynx-Trachea, etc., patents such as U.S. Pat. Nos. 4,596,579, 4,586,931, 4,494,252, 4,439,872, etc. bear no prior art. Likewise under Subclasses 433/19 and 433/06 for Orthodontal, patents such as U.S. Pat. Nos. 4,551,095, 4,472,139 and 138, 4,462,800, etc. and 4,580,975, 4,568,280, 4,541,800, 4,516,936, etc., respectively, show no prior art. This is not surprising since may invention is one of a new art in OSA.

A BRIEF DESCRIPTION OF THE DRAWING FIGURES

FIG. 1. The Top View of the invention showing the configuration of the appliance device, the front beak and clamps.

FIG. 2. Likewise for the Bottom View.

FIG. 3. The Front View showing clearly the airway orifice through the beak, the supporting clamps.

FIG. 4. A typical Side View showing the unique one-piece configuration unlike two-piece prior art, the clamps and the deep lower flange of the appliance.

FIG. 5. The Rear View of the appliance.

FIG. 6. A Section cut through the Beak and Airway Orifice.

LEGEND OF NUMBERS USED ON THE DRAWINGS

1 Palatal flange of the appliance body
2 Buccal (cheek side) of the appliance
3 Maxillary teeth depressions (upper)
4 Labial arch wires
5 Maxillary molar wire clasp (upper)
6 Top of oral beak
7 Mouth of oral beak
8 Lingual flange of appliance body (lower)
9 Anterior lingual flange of appliance body
10 Mandibular teeth depressions (lower)
11 Mandibular molar clasp (lower)
12 Underside of oral beak
13 Airway orifice of oral beak

A BRIEF DESCRIPTION OF THE INVENTION

The invention is essentially a one-piece intra-oral device, unlike any prior art two-piece devices such as orthodontal dentures and the like, which is worn to sleep by patients with sleep apnea to prevent occlusion of the oral airway passage and its potential life threatening consequences.

The main objective of the invention is to devise a less expensive mechanical solution to insure nocturnal breathing in lieu of expensive and painful surgery or therapy by the use of drugs with its side effects and inconveniences.

Another objective is to provide a comfortable and chemically neutral pleasant mouthpiece to be worn throughout the nocturnal period.

Still another objective is to ensure that the mouthpiece appliance will be retained in place comfortably.

One important objective is to keep the lips of the patient apart to ensure that the airway passage will always be open for fresh air.

The appliance device must also depress the tongue and constrain it from blocking the larynx.

My new and unique invention is configured to meet these objectives. Other features will become apparent in the description of the embodiments below. It features are not limited to these embodiments since the configuration may be altered by varying the material, size and shape to function the same.

DETAIL DESCRIPTION OF THE EMBODIMENTS OF THE INVENTION

The embodiments of the invention consist of a one-piece mouthpiece appliance more specifically labeled as the Palatal Flange 1 and the Buccal or Cheek sides 2 of the body of the appliance as shown in FIG. 1. On the upper side of the palatal flange 1 are the custom molded Maxillary Teeth Depressions 3 to receive the patient's teeth comfortably; the Labial Arch Wires 4 at the front perimeter of the teeth and the Maxillary Molar Clasps 5 toward the ends of the row of teeth. The front of the mouthpiece appliance is configured into a lip-parting Oral Beak 6 with an orifice Mouth 7 at the front end. The mouthpiece appliance may be made of orthdontally acceptable molding plastics like acrylic or other materials of the state of the art.

FIG. 2 is the Bottom View of the appliance showing likewise respective parts like the lower Lingual Flange 8 of the body and the Anterior Lingual Flange 9 toward the front end and the lower Mandibular Teeth Depressions 10 with the Mandibular Molar Clasps 11 only at the rear ends. The under side of the Oral Beak 12 is an integral part of the body.

FIG. 3 is a Front View of the appliance showing more clearly the profiles of the labial arch wires 4, the molar clasps 5 and 11 in relation to the body of the appliance and its palatal flanges 1 and anterior linqual flange 9. The configuration of the orifice mouth 7 of the oral beak is outlined by the top side 6 and the underside 12 of same.

FIGS. 4 and 5 shows the same elements of FIG. 3 from the Typical Side View and from the Rear View respectively.

FIG. 6 is a Sectional View of a cut through the center of the appliance body showing the same elements more clearly with Airway Orifice 13 of the oral beak profiled. It is to be noted that the configuration of all the elements from 1 to 12 is normally custom fitted to each patient's oral cavity and gum-teeth profiles. The lingual flanges 8 and 9 are key elements to depress and constrain the tongue of the patient comfortably to prevent occlusion of the breathing passage. This sectional view illustrates most clearly the unique features of my invention which is a new and novel mechanical solution to meet the objectives described earlier.

I claim:

1. A preformed device consisting of a one-piece mouthpiece of orthodontal plastics said device having upper and lower negative impressions which are so configurated so as to fit a patient's mouth's upper and lower teeth; said device having an inward and outward flange extending from said impressions; said device has embedded therein fitted labial arch wire guides along the front upper perimeter of the teeth; and molar wire clasps at the rear on each side of both upper and lower teeth of the outward flange body of the appliance; and with a lip-parting beak integrally molded at the front end of the appliance body with an air-way orifice passage through the same beak.

* * * * *